US009339287B2

(12) United States Patent
Hassoun

(10) Patent No.: US 9,339,287 B2
(45) Date of Patent: May 17, 2016

(54) SURGICAL INSTRUMENT

(76) Inventor: Basel Hassoun, Oklahoma City, OK (US)

(*) Notice: Subject to any disclaimer, the term of this patent is extended or adjusted under 35 U.S.C. 154(b) by 642 days.

(21) Appl. No.: 13/580,353

(22) PCT Filed: Mar. 3, 2011

(86) PCT No.: PCT/US2011/027061
§ 371 (c)(1),
(2), (4) Date: Aug. 21, 2012

(87) PCT Pub. No.: WO2011/109640
PCT Pub. Date: Sep. 9, 2011

(65) Prior Publication Data
US 2012/0316560 A1 Dec. 13, 2012

Related U.S. Application Data

(60) Provisional application No. 61/309,999, filed on Mar. 3, 2010.

(51) Int. Cl.
A61B 18/18 (2006.01)
A61B 17/29 (2006.01)
A61B 17/00 (2006.01)
A61B 19/00 (2006.01)

(52) U.S. Cl.
CPC ... *A61B 17/2909* (2013.01); *A61B 2017/00314* (2013.01); *A61B 2017/00327* (2013.01); *A61B 2017/2902* (2013.01); *A61B 2017/2927* (2013.01); *A61B 2019/2242* (2013.01); *A61B 2019/2292* (2013.01)

(58) Field of Classification Search
CPC .................................................. A61B 17/2909

USPC ........................................................... 606/52
See application file for complete search history.

(56) References Cited

U.S. PATENT DOCUMENTS 4,374,481 A 2/1983 Brodie
5,281,220 A 1/1994 Blake, III
5,395,367 A 3/1995 Wilk
5,752,973 A 5/1998 Kietarakis
(Continued)

FOREIGN PATENT DOCUMENTS

EP 0646356 A2 5/1995
EP 2151204 A1 10/2010
(Continued)

OTHER PUBLICATIONS

International Search Report and Written Opinion in PCT/US2011/027061, dated May 5, 2011, Hassoun, Basel.
(Continued)

*Primary Examiner* — Carl H Layno
*Assistant Examiner* — Jennifer Ghand
(74) *Attorney, Agent, or Firm* — McAfee & Taft, A Professional Corporation

(57) ABSTRACT

A surgical apparatus for use in endoscopic surgery having a user interface operatively coupled to an articulating tool assembly via an elongate tubular member. Movement at the articulating tool mirrors movement at the user interface thereby providing intuitive operation of the surgical apparatus. The apparatus is configured such that the range of motion of the articulating tool assembly emulates the range of motion of the human wrist.

20 Claims, 13 Drawing Sheets

(56) References Cited

U.S. PATENT DOCUMENTS

| | | |
|---|---|---|
| 5,755,713 A | 5/1998 | Bilof et al. |
| 5,766,205 A | 6/1998 | Zvenyatsky et al. |
| 5,823,066 A | 10/1998 | Huitema et al. |
| 5,984,939 A | 11/1999 | Yoon |
| 6,461,372 B1 | 10/2002 | Jensen et al. |
| 6,506,208 B2 | 1/2003 | Hunt et al. |
| 6,656,205 B1 | 12/2003 | Manhes |
| 7,273,488 B2 | 9/2007 | Nakamura et al. |
| 7,470,276 B2 | 12/2008 | Tu |
| 7,544,197 B2 | 6/2009 | Kelsch |
| 7,615,066 B2 | 11/2009 | Danitz et al. |
| 2005/0187575 A1 | 8/2005 | Hallbeck et al. |
| 2006/0111210 A1 | 5/2006 | Hinman |
| 2007/0106317 A1 | 5/2007 | Shelton, IV et al. |
| 2007/0225562 A1 | 9/2007 | Spivey et al. |
| 2007/0250113 A1* | 10/2007 | Hegeman et al. ............ 606/207 |
| 2008/0015631 A1 | 1/2008 | Lee et al. |
| 2008/0255420 A1 | 10/2008 | Lee |
| 2008/0262513 A1 | 10/2008 | Stahler et al. |
| 2009/0171147 A1 | 7/2009 | Lee |
| 2012/0220831 A1 | 8/2012 | Cooper et al. |

FOREIGN PATENT DOCUMENTS

| | | |
|---|---|---|
| WO | WO 2006073581 A2 | 7/2007 |
| WO | 2008/020964 A2 | 2/2008 |

OTHER PUBLICATIONS

Office Action in Chinese Application No. 201180012051.1, mailed Sep. 8, 2014, Hassoun, Basel.

Examiner's First Report in Australian Patent Application No. 2011223525, mailed Jun. 10, 2013, Hassoun, Basel.

International Preliminary Report on Patentability in PCT/US2011/027061, dated Sep. 21, 2012, Hassoun, Basel.

Office Action in Chinese Application No. 20118001205.1, mailed Apr. 28, 2015, Hassoun, Basel.

European Search Report in European Application No. 11751372.1, mailed Jul. 13, 2015, Hassoun, Basel S.

* cited by examiner

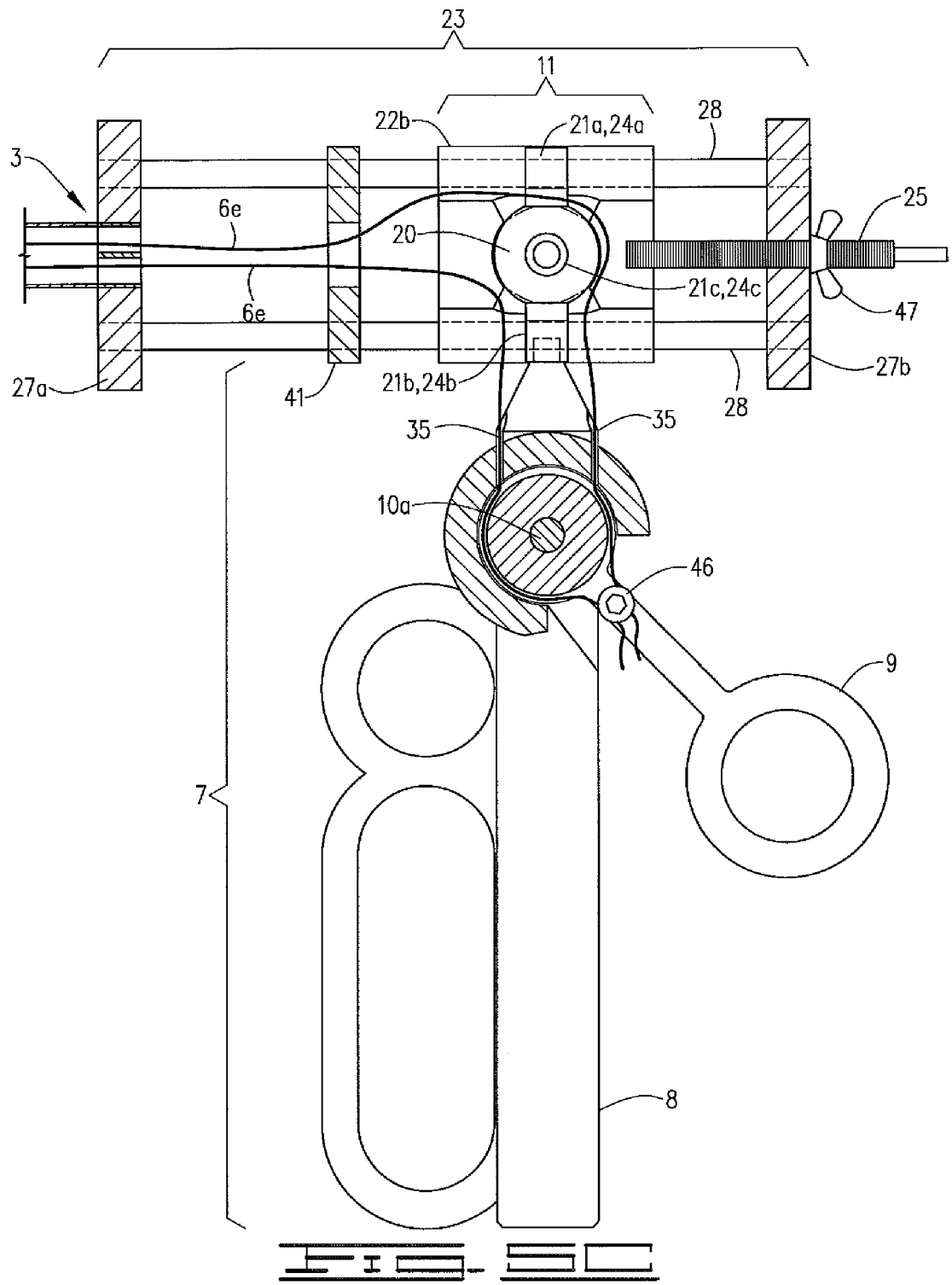

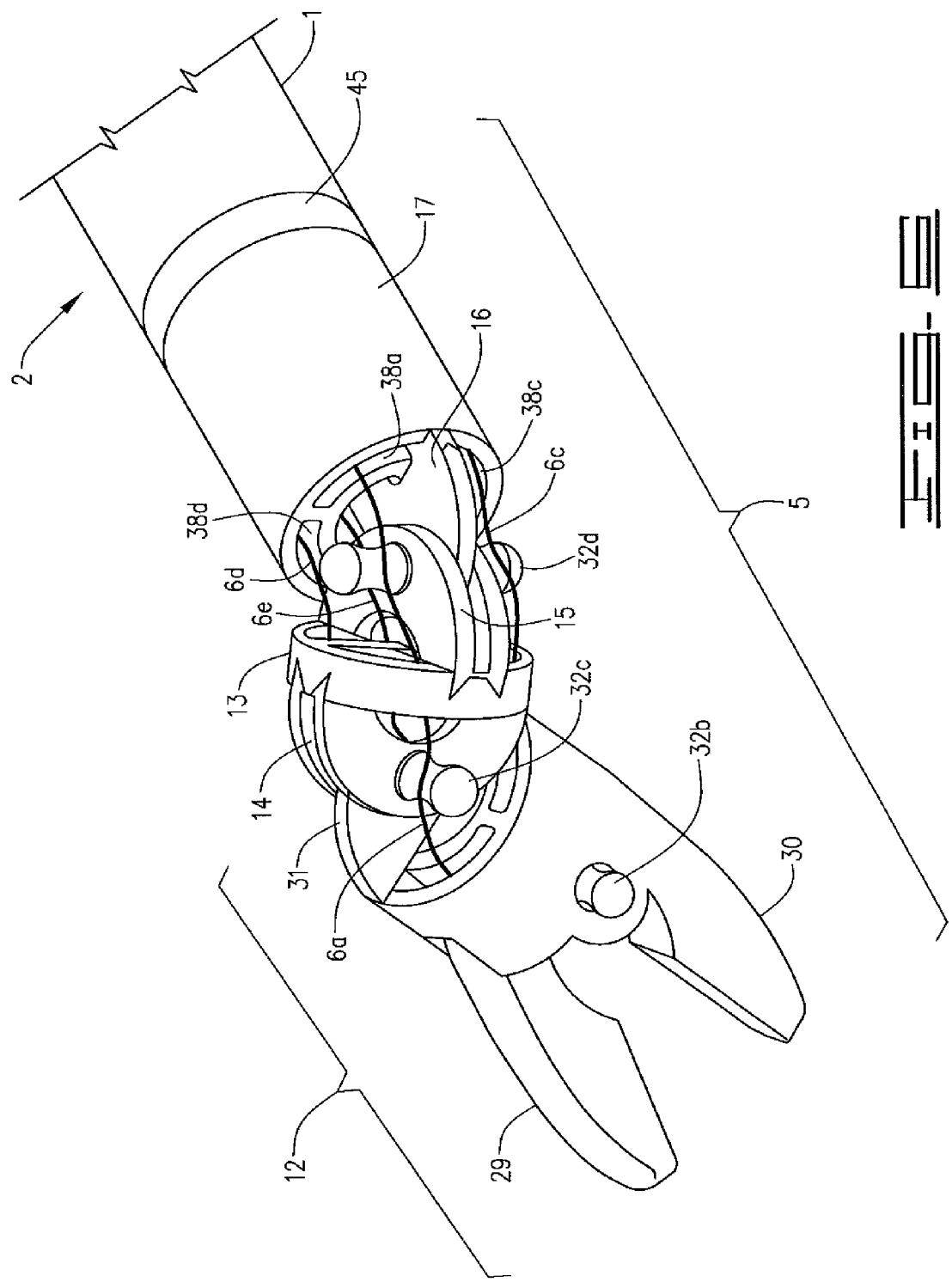

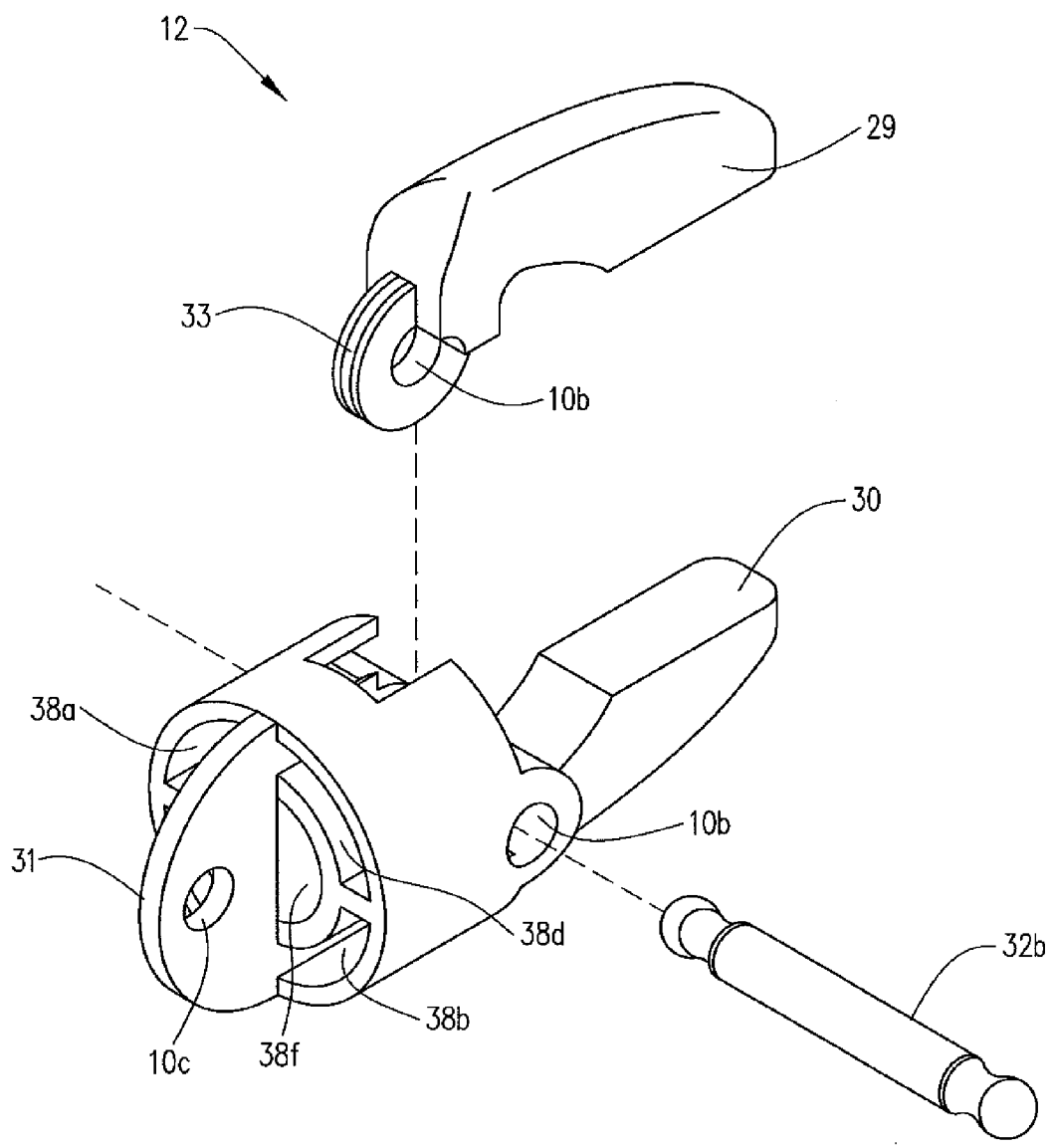

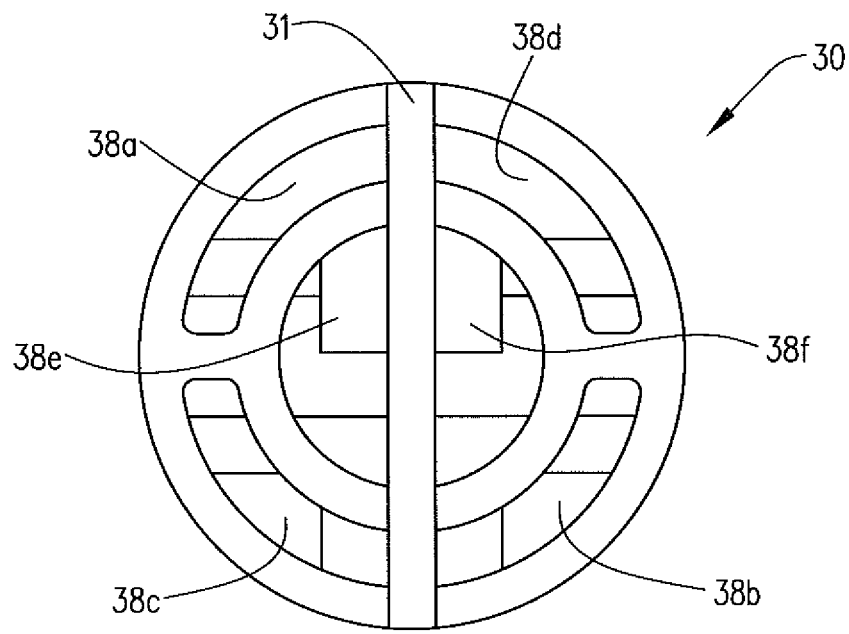
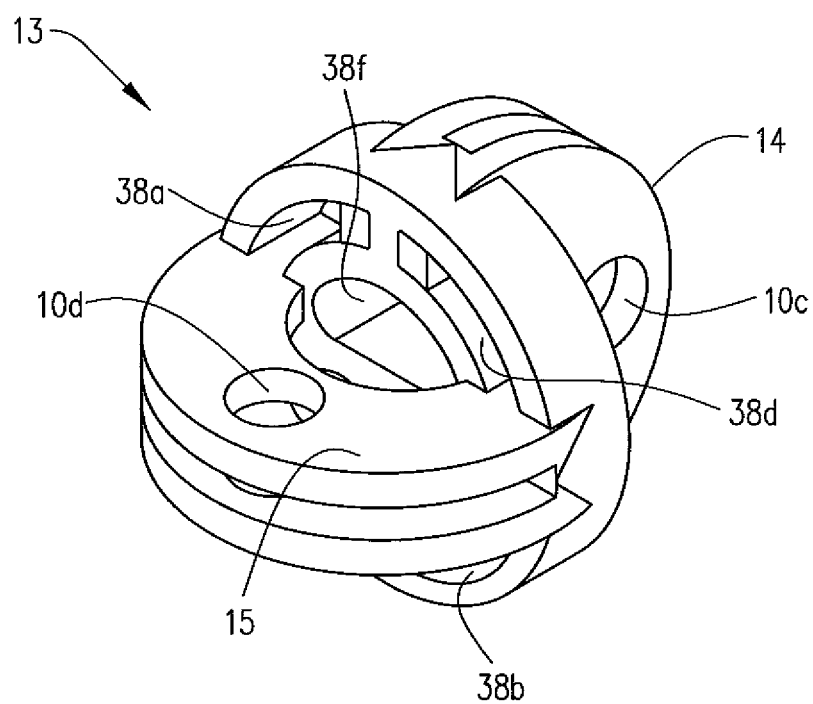

SURGICAL INSTRUMENT

RELATED APPLICATION

This application claims the benefit of International Application No. PCT/US2011/027061 filed on Mar. 3, 2011, which claims the benefit of U.S. Provisional Application No. 61/309,999 filed on Mar. 3, 2010, which are hereby incorporated by reference in their entirety.

BACKGROUND

Minimally invasive surgery (MIS), such as laparoscopic surgery and thoracoscopic surgery are specialized types of surgery in the broader field of endoscopy. Laparoscopic surgery includes operations within the abdominal and pelvic cavities; thoracoscopic surgery includes operations within the thoracic cavity. Various tools and instruments are utilized during these procedures.

Such tools for MIS include robotic assisted instruments and various forms of hand-operated instruments. Unfortunately, robotic assisted instruments require extensive training, are expensive and bulky. Additionally, some hand-operated instruments are counter-intuitive, i.e. movement in the tool end is opposite from movement at the user interface or actuation end. For instance, when the operator moves the user interface right, the tool end moves left. Like the counter-intuitive instruments, intuitive hand-operated instruments have limited mobility and flexibility. Movements are more discrete, such as left, right, up, down; however, these devices do not provide transitional movement through all angular ranges. Thus, in order to obtain further articulation of the tool end, the user must physically reposition him/herself and/or the instrument.

SUMMARY

The instrument described herein provides an intuitive hand-operated instrument that provides tactile feedback capable of intricate movements with a range of motion comparable to that of a human wrist. Further, the instrument described herein is a low cost, reliable, portable instrument that is safe for use in surgery, durable for repeated use, adaptable to the physical limitations of various procedures, and is easy to learn and use.

In one embodiment, the current invention is a surgical instrument including a user interface operatively coupled to an articulating tool assembly through an elongate tubular member having a distal end and a proximal end. The user interface is coupled to the proximal end of the elongate tubular member and the articulating tool assembly coupled to the distal end of the elongate tubular member. At least one cabling member extends through the elongate tubular member connecting the user interface and the articulating tool assembly such that movement of the user interface causes corresponding movement in the same direction of the user interface at the articulating tool assembly.

The objects, features and advantages of the instrument will be readily apparent to those skilled in the art upon a reading of the description of preferred embodiments which follows when taken in conjunction with the accompanying drawings.

BRIEF DESCRIPTION OF THE DRAWINGS

FIG. 5c is a side cross sectional view of another embodiment of the user interface.
FIG. 6 shows one embodiment of the articulating tool assembly.
FIG. 8 is an exploded isometric view of the back of the tip assembly.
FIG. 9 is a cross sectional view of the back of base member of the tip assembly.
FIG. 10 is an isometric view of the dual hinge member of the articulating tool assembly.

DETAILED DESCRIPTION

Figure 1:
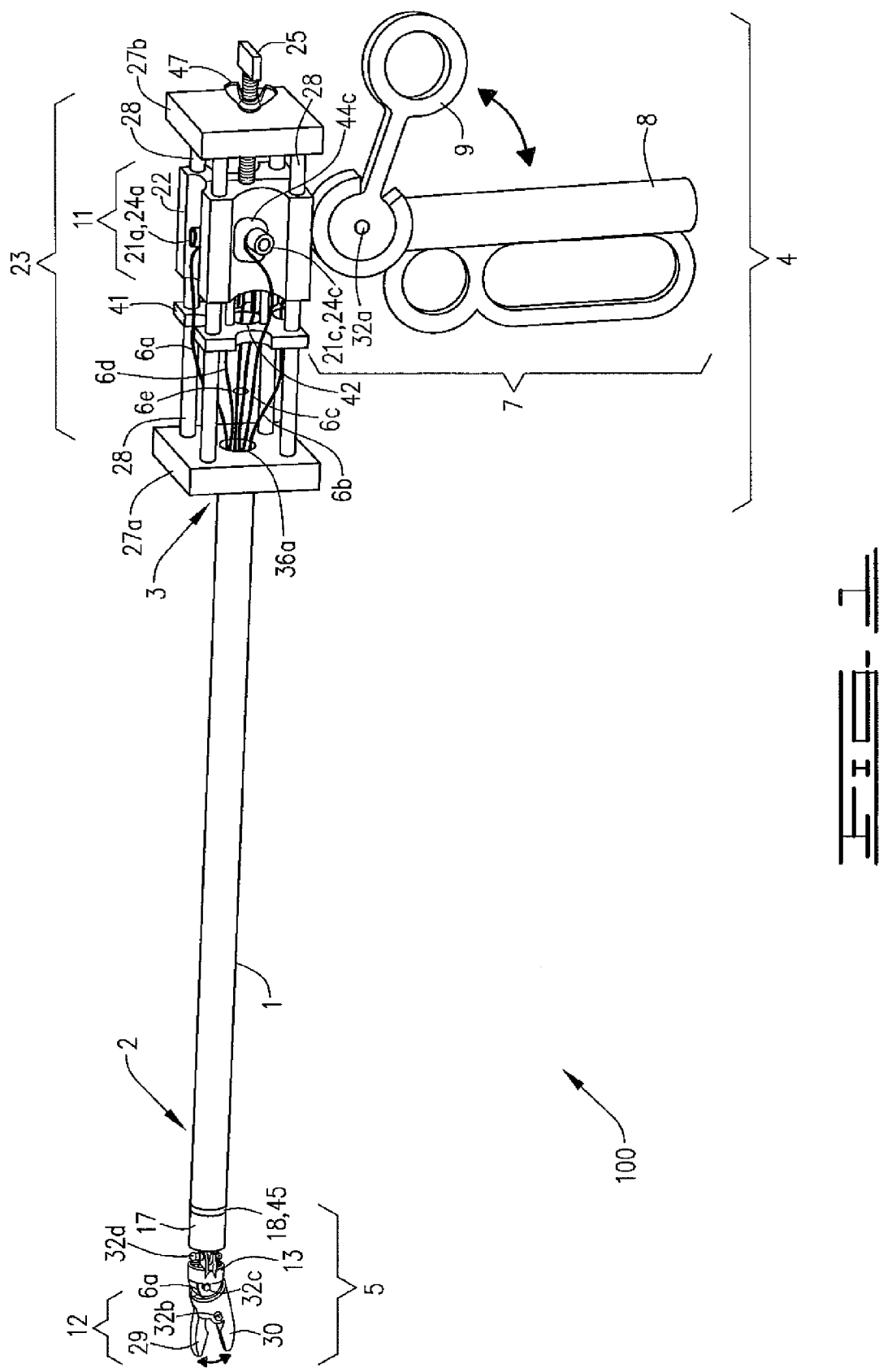
FIG. 1 is a side view of the instrument.
Figure 2:
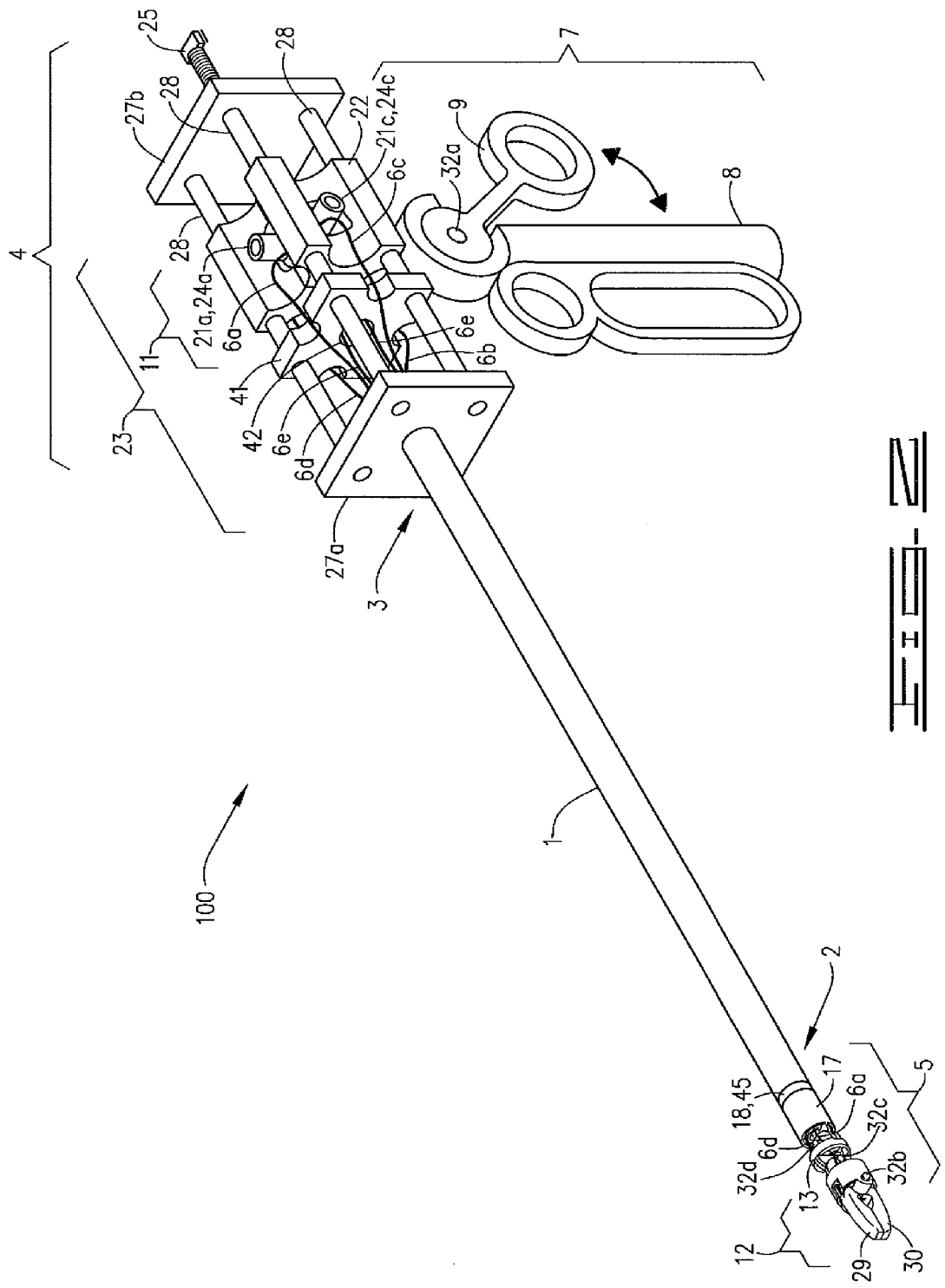
FIG. 2 is an isometric view of the instrument.

FIGS. 1 and 2 depict a side view and isometric view, respectively, of instrument 100. Instrument 100 may be manufactured from any suitable surgically safe materials such as but not limited to stainless steel, aluminum, titanium, plastics and composites. Instrument 100 includes elongate tubular member 1 having a distal end 2 and a proximal end 3. Instrument 100 also includes user interface 4 coupled to proximal end 3, and an articulating tool assembly 5 coupled to distal end 2. User interface 4 is operatively connected to articulating tool assembly 5 by at least one cabling member 6 extending through elongate tubular member 1. User interface 4 controls or manipulates articulating tool assembly 5 such that movement at user interface 4 is translated to articulating tool assembly 5. The range of motion of articulating tool assembly 5 is comparable to that of the human wrist.

Instrument 100 provides one-handed operation and direct tactile sensations transmitted to the user during use. Since user input or movement of user interface 4 provides identical mirror like movement of articulating tool assembly 5, instrument 100 is intuitive and easy to learn and operate. Instrument 100 will normally be used in a variety of fields where the distal end 2 and articulating tool assembly 5 will be separated from the user interface 4 by a barrier. Typically, articulating tool assembly 5 will be disposed within a cavity, for example but not limited to, an anatomical cavity (not depicted), with user interface 4 disposed external to the cavity. In a preferred embodiment, instrument 100 is used for performing open surgical procedures and endoscopic procedures such as laparoscopic and thoracoscopic surgeries on human subjects and veterinary subjects.

Figure 3:
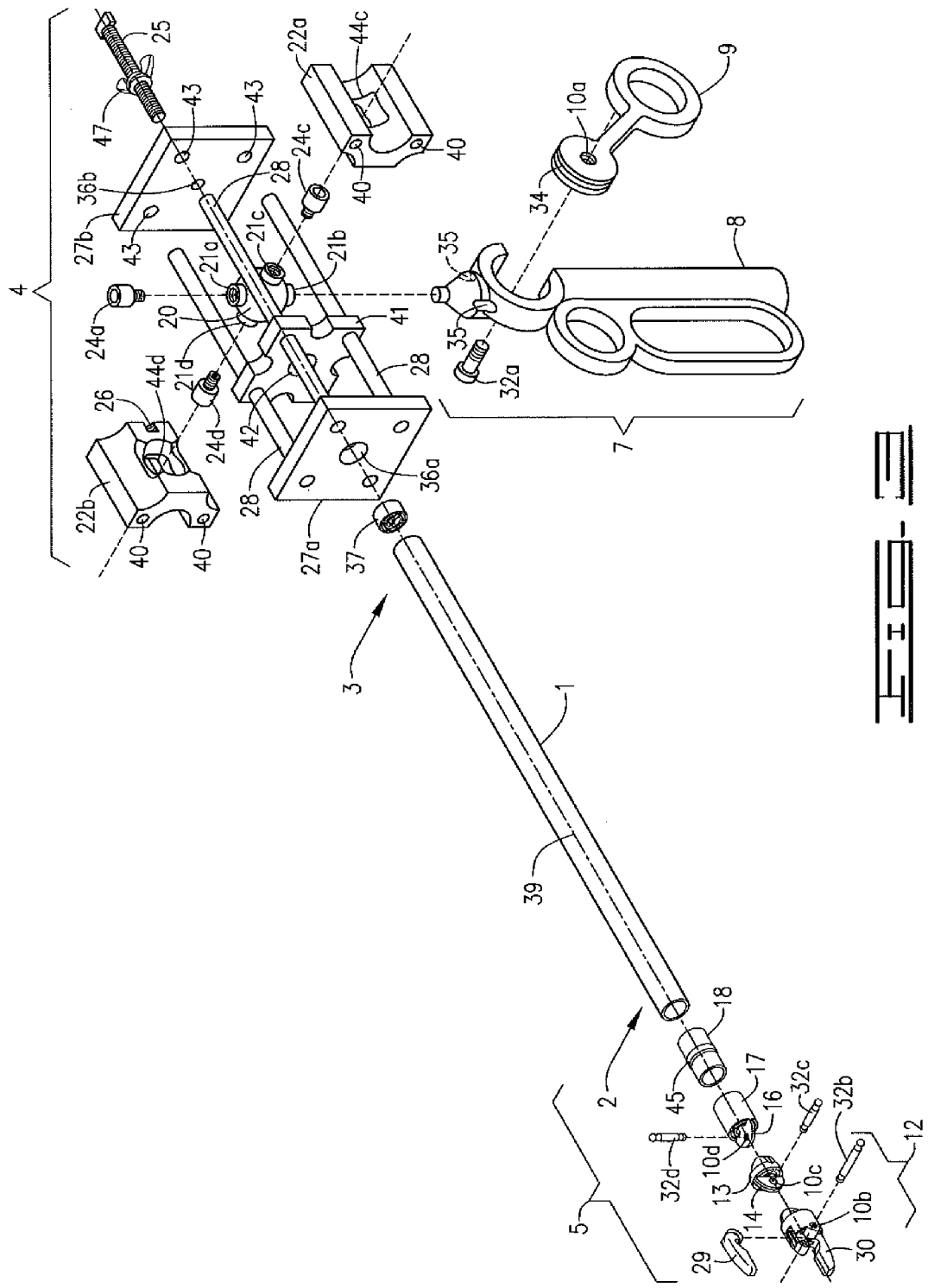
FIG. 3 is an exploded view of the instrument.
Figure 4:
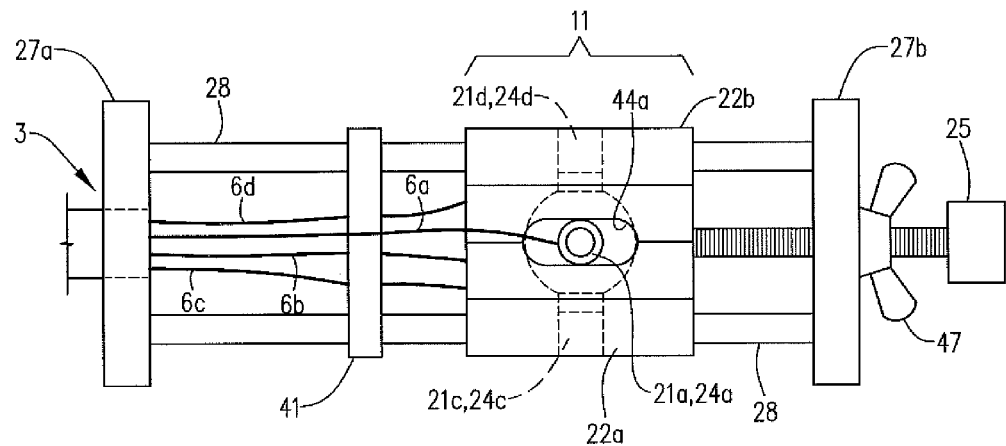
FIG. 4 shows a top view of the support assembly.

FIG. 3 is an exploded view of one embodiment of instrument 100. Turning first to user interface 4 as depicted in FIGS. 1-3, user interface 4 includes handle assembly 7 operatively coupled to ball and socket assembly 11, and a support assembly 23. Support assembly 23 includes first and second end walls 27a, 27b, and support rails 28 extending therebetween.

First and second end walls 27a, 27b are made of material suitable for use in surgery. However, a sample instrument 100 suitable for teaching and demonstration purposes, may use a lightweight, transparent material, such as a transparent thermoplastic, for example poly(methyl methacrylate) in place of the standard surgical end walls 27. End walls 27 have an approximate height and width ranging from about 30 mm to about 60 mm with a preferred height and width of about 50.04 mm (1.97 in) with a thickness of ranging from about 8 mm to about 25.4 mm with a preferred thickness of about 20.07 mm (0.79 in). Support rails 28 are received in cavities 43 having a diameter 5.08 mm (0.20 in) on the periphery of end walls 27. Support rails 28 are press fitted into the receiving cavities 43 on end walls 27a, 27b. In another embodiment, support assembly 23 is completely encased, such that the various components positioned on support rails 28 are not visible. Overall, the length of support assembly 23 is approximately 110 mm to 150 mm with a preferred length of about 139.70 mm (5.50 in) with a height and width ranging from about 30 mm to about 60 mm and a preferred height and width of approximately 50.04 mm (1.97 in). In a preferred embodiment, the bottom side of second end wall 27b is contoured to complement the natural curve of the user's forearm.

Figure 13:
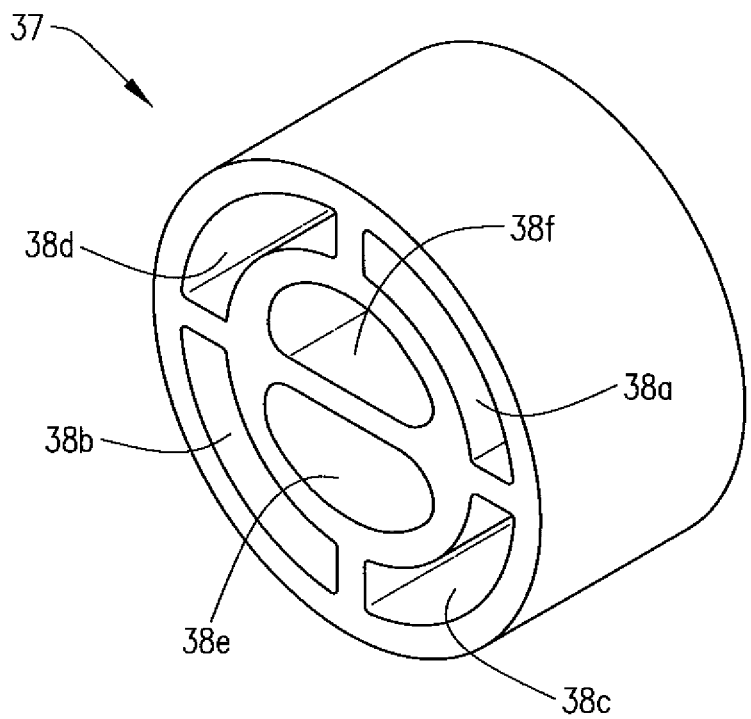
FIG. 13 is an isometric view of the guide member.
Figure 14:
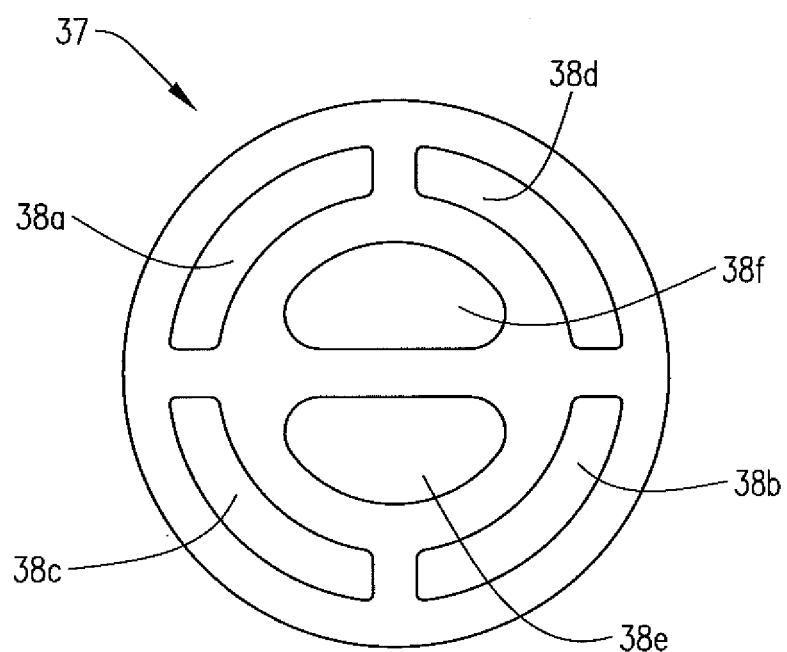
FIG. 14 is a cross sectional view of the guide member.

End walls 27a, 27b both have central bores 36a, 36b, respectively. Central bore 36a provides an attachment site for securing elongate tubular member 1 to user interface 4. Elongate tubular member may be secured to interface 4 by any convenient means including but not limited to a press fit within bore 36a or threaded into bore 36a. Additionally, central bore 36a provides a passage for cabling members 6a, 6b, 6c, 6d, and 6e, to enter elongate tubular member 1. Also depicted in FIGS. 3, 13, and 14 is guide member 37 having guide cavities 38a, 38b, 38c, 38d, 38e, and 38f Guide member 37 may be positioned at any convenient location, including but not limited, to within central bore 36a or within the interior of tubular member 1. Alternatively, guide member 37 may be secured to first end wall 27a, axially with bore 36a, and may act as an attachment point for tubular member 1. Guide member 37 provides each cabling member 6 an isolating cavity 38. Isolating cavity 38 acts as a guide isolating cable members 6 from one another thereby precluding entanglement of cabling members 6. Preferably, guide member 37 is made from stainless steel and has an approximate diameter ranging from about 5 mm to about 15 mm with a preferred diameter of about 12 mm (0.47 in) and is located inside the proximal end 3 of elongate tubular member 1. In a preferred embodiment, guide member 37 is press fitted until flush within proximal end 3 of elongate tubular member 1. Elongate tubular member 1 is made from stainless steel and preferably has an outside diameter of about 5 mm to about 12 mm with a preferred outside diameter of 12 mm (0.47 in), an inner diameter of about 4 mm to about 11 mm with a preferred inner diameter of 11 mm (0.43 in) and length of about 304.8 mm to about 457.2 mm with a typical length of about 304.8 mm (12 in) depending upon the procedure to be performed.

In a preferred embodiment, the ball and socket assembly 11 is slideably positioned on support rails 28 with socket 22 carried on support rails 28 passing through passages 40. The slideable configuration permits positioning and securing of ball and socket assembly 11 along support rails 28 based on user preference. For example, positioning ball and socket assembly 11 near the center of support assembly 23 provides more flexibility to the user in adjusting the cable tension. For example, turning locking rod 25 clockwise causes the ball and socket assembly 11 to move closer to second end wall 27b, thereby increasing the tension in cabling member 6. Handle assembly 7 is directly coupled to the ball and socket assembly 11 for direct transference of movement of handle assembly 7 to the articulating tool assembly 5 via cabling member 6.

As shown in FIG. 3, central bore 36b allows for locking rod 25 to extend through second end wall 27b to secure the ball and socket assembly 11 at the desired location on the support assembly 23. In one embodiment, locking rod 25 is a ¼ in—20NC bolt with a length of approximately 38.1 mm (1.5 in) to 50.8 mm (2.0 in). In the preferred embodiment, a threaded recess 26 carried by each half 22 of socket assembly 11 forms a threaded bore for receiving threaded locking rod 25. The threaded engagement between locking rod 25 and socket assembly 11 provides the ability to adjust the tension of cabling members 6 by moving socket assembly 11 towards or away from second end wall 27b. Additionally, locking rod 25 carries a wing nut 47. Following setting of the desire tension, tightening of wing nut 47 against the exterior of second end wall 27b fixes the relationship of locking rod 25 and socket assembly 11 thereby maintaining the desired tension on cabling members 6.

Figure 15:
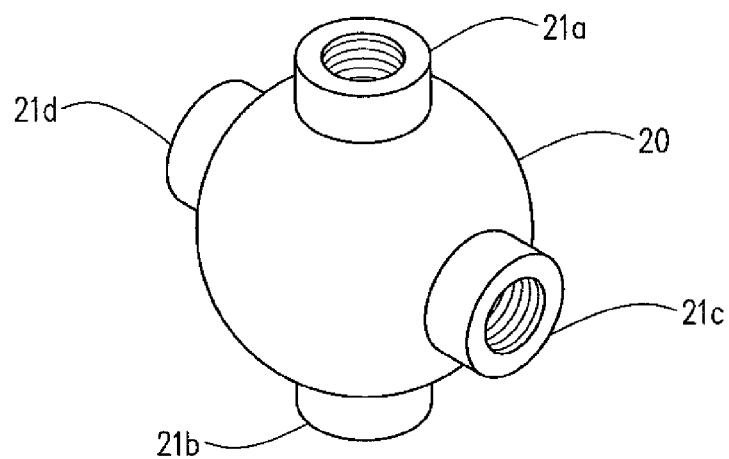
FIG. 15 is an isometric view of the ball of the ball and socket assembly.

As depicted in FIGS. 1-3, ball and socket assembly 11 is positioned on support assembly 23. Ball and socket assembly 11 includes ball 20, depicted in FIGS. 3 and 15. Generally spherical in shape, ball 20 has top, bottom, left, and right protruding arms 21a, 21b, 21c, and 21d, respectively. In a preferred embodiment, protruding arms 21 are cylindrical in shape; however, arms 21 can be any suitable shape for coupling cabling member 6 to ball 20. In one embodiment ball 20 has a diameter of about 15 mm to about 25 mm. Typically, the diameter of ball 20 will be about 19 mm (0.75 in). Preferably, ball 20 is made of stainless steel. Each protruding arm 21 provides an attachment point for one cabling member 6 (6a, 6b, 6c, and 6d).

Cabling members 6 should be prepared from material that is strong and surgically safe. Suitable material includes but is not limited to 304 stainless steel nylon coated cable. Any similar component suitable for operatively coupling user interface 4 with articulating tool assembly 5 will perform satisfactorily in the current invention, such similar component can be used in, for example, non-surgical procedures such as training or demonstrative purposes. Securing member 24 can be any suitable device known in the art, for example, bolts, pins, buttons, press-fitted pins, and screws or any similar component suitable for securing cabling member 6 to protruding arms 21a, 21c, and 21d will perform satisfactorily in the current invention. In a preferred embodiment, protruding arms 21a, 21b, 21c, and 21d are internally threaded to receive securing member 24, for example, a screw. In the preferred embodiment, both securing member 24 and locking rod 25 provide the ability to adjust the tension of cabling member 6. In this embodiment, manipulation of securing member 24 can either increase or decrease tension on cabling member 6. Alternatively, cabling member 6 is attached directly to protruding arms 21a, 21b, 21c, and 21d by any convenient arrangement, such as but not limited to, tying or soldering. In the preferred embodiment, support assembly 23, including locking rod 25 will be enclosed in an aesthetically pleasing shroud or cover (not shown).

Referring to FIGS. 1, 2, 4, 5B, 5C, 15 and 16, ball 20 is disposed within a spherical cavity formed by socket members 22a, 22b of socket 22. Assembled socket 22 has openings 44 to receive protruding arms 21a, 21b, 21c, and 21d to permit unobstructed movement of ball 20 within socket 22. This configuration provides the optimal range of movement for ball 20. As discussed above, this range of movement translates directly to articulating tool assembly 5.

In one embodiment, top and bottom openings 44a, 44b (only one depicted) of socket 22 through which top and bottom protruding arms 21a, 21b project are generally elliptical in shape thereby restricting the range of motion of the top and bottom protruding arms. However, the openings 44c, 44d through which left and right protruding arms 21c, 21d project are generally rectangular in shape thereby permitting a full range of left and right movement with respect to the location of the top and bottom protruding arms 21a, 21b.

Figure 16:
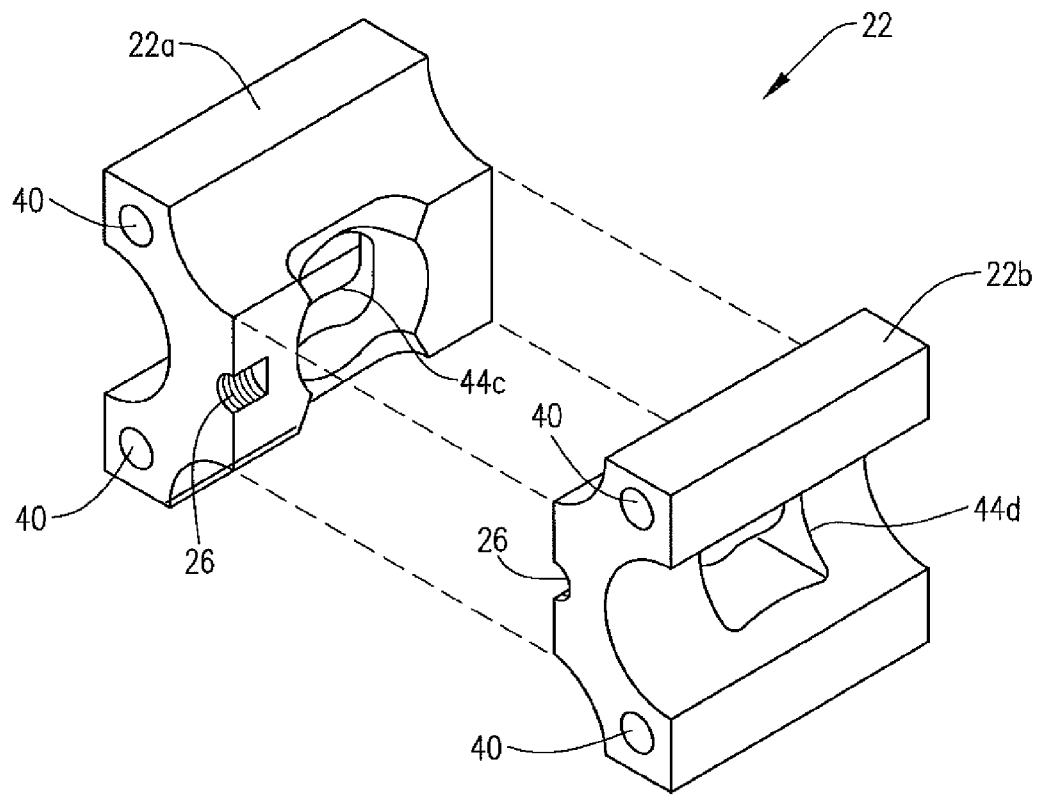
FIG. 16 is an isometric view of the back of the socket members of the ball and socket assembly.

As shown in FIGS. 2 and 16, the preferred embodiment utilizes a socket 22 with a periphery having a generally "X" shaped configuration with recessed portions defining an arcuate concave surface. The arcuate concave surface prevents cabling member 6 from becoming lodged or stuck at the apex of the recessed portions. The dimensions and material of socket 22 can vary per application; in one preferred embodiment socket 22 is made of stainless steel having outermost dimensions of 40 mm (1.57 in) long, 40 min (1.57 in) wide and 40 mm (1.57 in) deep. However, socket 22 may have a length ranging from about 25 mm to about 50 mm, a width ranging from about 25 mm to about 50 mm and a depth ranging about 25 mm to about 50 mm.

Similarly and for the same reasons of socket 22, slide block 41 preferably has a generally "X" shaped periphery. Slide block 41 is positioned on the support rails 28 between first end wall 27a and ball and socket assembly 11. In a preferred embodiment, slide block 41 is slideably mounted on support rails 28. Slide block 41 provides support for cabling 6 and channels cabling 6 to elongate tubular member 1. In one embodiment, slide block 41 is made of stainless steel and is 40 mm (1.57 in) wide, 40 mm (1.57 in) long and has a thickness of 6.5 mm (0.25 in). However, slide block 41 may have a width ranging from about 25 mm to about 50 mm, a length ranging from about 25 mm to about 50 mm and a thickness ranging from about 8 mm to about 25.4 mm.

In a preferred embodiment, handle assembly 7 includes grip member 8 and lever member 9 pivotally coupled to grip member 8 at pivot point 10a. Preferably, grip member 8 and lever member 9 will be ergonomically designed to comfortably fit within the surgeon's hand. In one embodiment grip member 8 is 162.6 mm (6.4 in) long with a diameter of 19 mm (0.75 in) and is made of metal, metal alloys, plastics and composites. In this embodiment, lever member 9 is 94 mm (3.7 in) long and made of metal, metal alloys, plastics and composites.

Grip member 8 is directly coupled to ball 20 at bottom protruding arm 21b, thereby directly translating movement of handle assembly 7 to ball and socket assembly 11. Lever member 9 actuates the opening and closing of tip assembly 12. Actuating lever member 9 counterclockwise and clockwise about pivot point 10a causes tip assembly 12 to move between fully closed and fully open and all positions therebetween.

In a preferred embodiment, articulating tool assembly 5 includes interchangeable tip assembly 12. Depending on the intended use of instrument 100, tip assembly 12 may be selected from any of the following non-limiting examples: graspers, dissectors, scissor and blade tip assemblies. To provide cauterization capabilities, one of the cabling members 6 (typically 6e) or an additional wire (not shown) provides an electrical current to the distal end of tip assembly 12. For cauterization purposes, the material forming the distal end of tip assembly 12 responds to the electrical current by producing heat sufficient to cauterize tissue. Except with regard to the distal end of tip assembly 12, the remaining portion of instrument 100, which comes into contact with tissue, will be insulated to protect the surrounding tissue from injury.

FIGS. 5A, 6, 7, and 8 depict a grasper embodiment of tip assembly 12. As shown, tip assembly 12 includes a moving member 29 pivotally connected to base member 30 at pivot point 10b with pivot fastener 32b. Pivot fasteners 32a, 32b, 32c, and 32d can be any fastener, suitable for operatively connecting the various components which are pivotally connected. Fasteners such as bolts, pins, buttons, press-fitted pins, and screws or any similar component will perform satisfactorily in the current invention.

To open tip assembly 12, the user will move actuating lever member 9 counterclockwise with respect to pivot point 10a. Conversely, to close tip assembly 12, the user will move actuating lever member 9 clockwise. In a preferred embodiment, lever member 9 and tip assembly 12 are operatively connected via cabling member 6e. As shown in FIGS. 1-5C and 8, a single cable 6e is positioned within a circumferential groove 34 of lever member 9 (FIG. 3), through holes 35 (only one depicted) of grip member 8, and extends through elongated tubular member 1 and loops around moving member 29 within circumferential groove 33 before extending back through elongated tubular member 1 to lever member 9. Thus, actuating lever member 9 causes moving member 29 of tip assembly 12 to move in relation to base member 30 about pivot point 10b. In this embodiment, cabling member 6e passes through the central bore 42 of slide block 41 and isolating cavities 38e and 38f as shown in FIGS. 5A-6 and 8-14. Cabling member 6e may be either a single continuous loop or a single strand with both ends of the strand secured to a convenient point 46 on lever member 9.

In another embodiment, cabling member 6e is shielded between handle assembly 7 and slide block 41 to prevent any entanglement of 6e with the other cabling members. With reference to FIGS. 8-14 and from the vantage point of looking down the longitudinal axis of elongate tubular member 1 from user interface 4, the cross sectional views of the various component pieces, e.g. base member 30, dual hinge member 13, elongate guide member 17, and guide member 37, align in a manner to confine cabling members 6 within each respective isolating cavity 38 thereby precluding entanglement with adjacent cabling members 6. It should be appreciated that the routing of cabling members 6 within isolating cavities 38, as depicted in the figures, is just one embodiment of the cabling configuration.

Figure 5A:
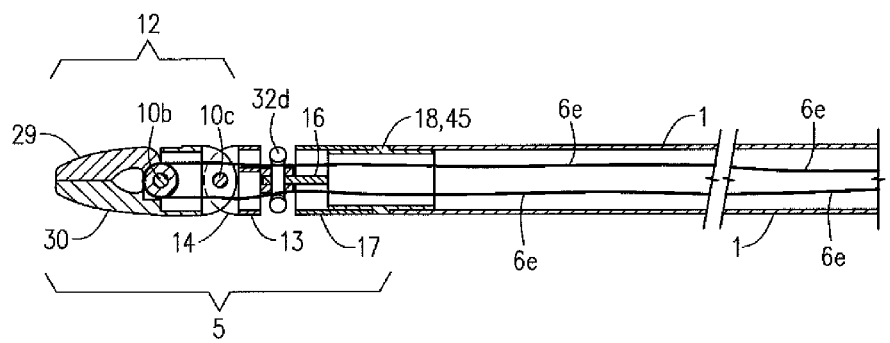
FIG. 5a shows a side cross sectional view of the articulating tool assembly and elongate tubular member of the instrument.
Figure 5B:
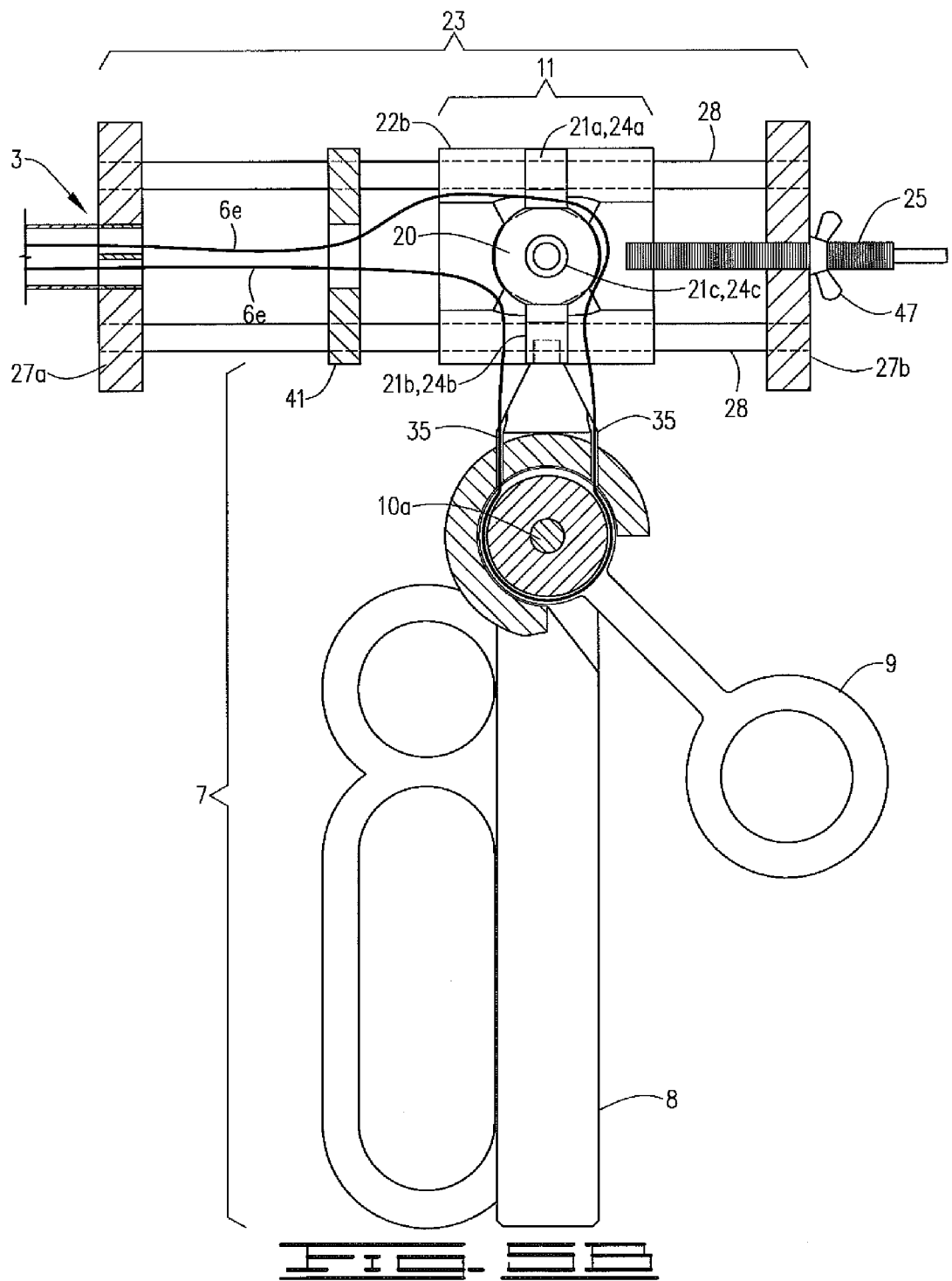
FIG. 5b is a side cross sectional view of the user interface of the instrument.
Figure 7:
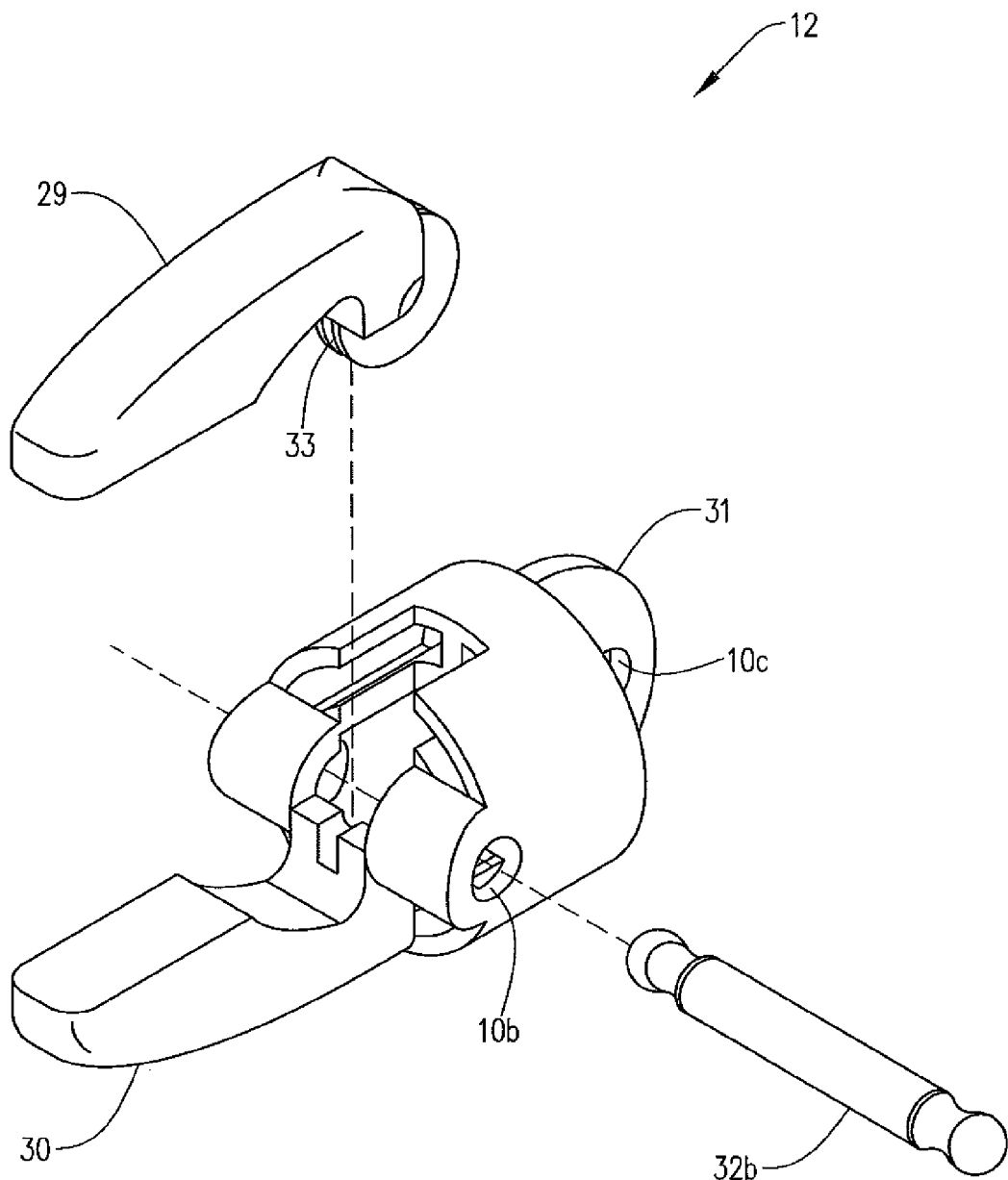
FIG. 7 an exploded isometric view of the front of the tip assembly.
Figure 11:
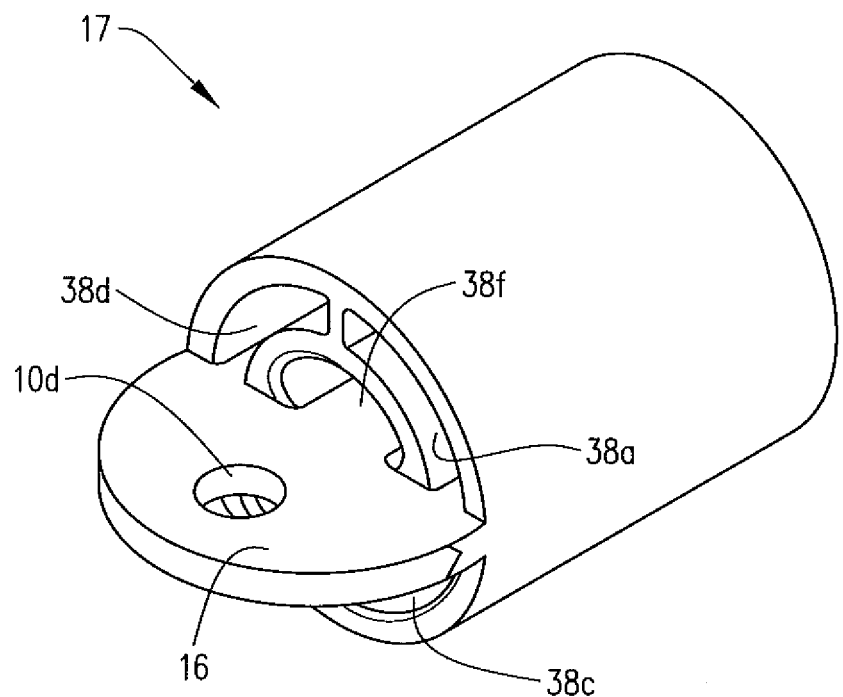
FIG. 11 is an isometric view of the elongate guide member of the articulating tool assembly.
Figure 12:
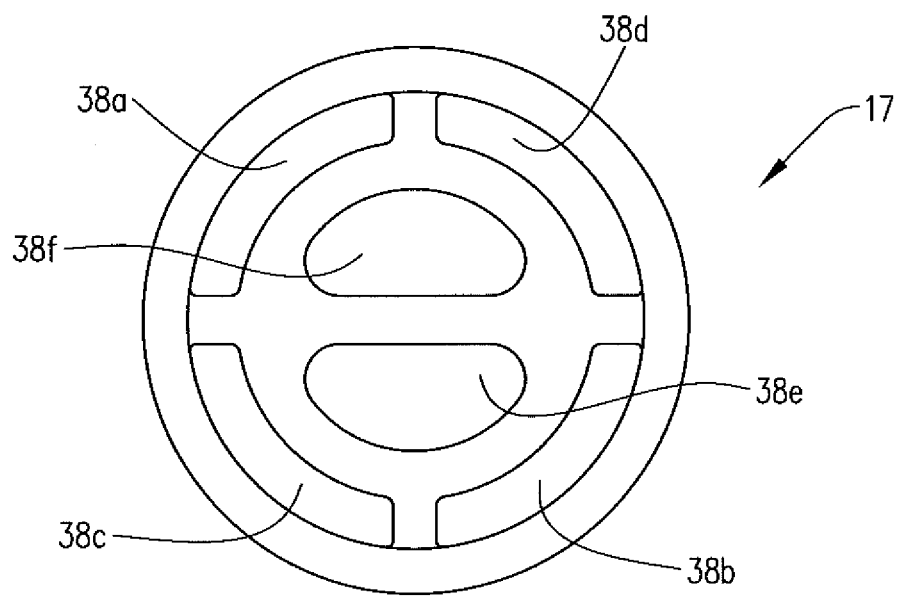
FIG. 12 is a cross sectional view of the elongate guide member.

Turning now to FIGS. 5A and 6, articulating tool assembly 5 also includes elongate guide member 17 and dual hinge member 13. Dual hinge member 13 has a first side 14 and a second side 15. See also FIGS. 10-12. Tip assembly 12 and elongate guide member 17 are pivotally coupled to dual hinge member 13 at pivot points 10c and 10d, respectively. The coupling provides a pivotal tongue and groove joint. As shown in FIGS. 6-8, tip assembly 12, specifically base member 30 has a "tongue." Base tongue 31 is a convex surface extending from the back of base member 30. In one embodiment base tongue 31 is in the form of a thin, outwardly projecting semi-circular member. A cross sectional view of the back of base member 30 is shown in FIG. 9. Base tongue 31 also has a through hole as pivot point 10c for pivotal coupling to dual hinge member 13. First side 14 of dual hinge member 13 carries the corresponding groove which receives base tongue 31. As shown in FIGS. 6 and 10, the first side 14 of dual hinge member 13 is two convex surfaces defining the groove for receiving base tongue 31. Likewise, first side 14 also has through holes for pivotal coupling to base member 30 with pivot fastener 32c. As depicted in FIG. 6, the operative coupling of base member 30 with dual hinge member 13 permits vertical movement, i.e. up and down movement, of tip assembly 12 with respect to the longitudinal axis 39 of elongate tubular member 1 as depicted in FIG. 3. For example, cabling members 6a and 6b, shown in FIGS. 1, 2 and 6 operatively connect to the top and bottom protruding arms 21a, 21b, respectively, of ball 20. When a user moves handle assembly 7, for example, forwards or backwards along longitudinal axis 39 of elongate tubular member 1, the tip assembly 12 vertically pivots about point 10c.

Pivot point 10d controls lateral movement, i.e. left and right movement, with respect to the longitudinal axis 39 of elongate tubular member 1. As depicted in FIG. 6, elongate guide member 17 is pivotally connected to the second side 15 of dual hinge member 13. Similar to the base member 30, elongate guide member 17 has elongate guide tongue 16, an outwardly projecting convex surface having a through hole for pivot point 10d. In the depicted embodiment, elongate guide tongue 16 is in the form of a thin outwardly projecting semi-circular surface. Likewise, the second side 15 of dual hinge member 13 is pivotally coupled to elongate guide tongue 16 to form a pivotal tongue and groove joint providing lateral movement.

For example, cabling member 6c and 6d, shown in FIGS. 1, 2, and 6, operatively connect to the left and right protruding arms 21c, 21d, respectively, of ball 20 to dual hinge member 13. As discussed above, the configuration of openings 44a, 44b, 44c, and 44d define the limits of movement for protruding arms 21. Thus, operation of handle assembly 7, for example twisting or rotating clockwise or counterclockwise with respect to support assembly 23 manipulates ball 20 within socket 22. For example, such manipulation translates down cabling 6c and 6d causing dual hinge member 13 to laterally pivot about point 10d. As already discussed and shown in FIGS. 3, 4, and 16, socket 22 has openings 44 to allow for protruding arms 21 to move unobstructed within a defined area. Lateral movement occurs as a result of the position of left and right protruding arms 21c and 21d, respectively.

It should be appreciated that the orientation of base tongue 31 and elongate tongue 16 are not limited to configuration described above. Other arrangements may be dictated by the nature of tip assembly 12 and the intended use thereof.

As shown in FIGS. 1-3, elongate guide member 17 is optionally coupled by joiner 18 to the distal end 2 of elongate tubular member 1. Joiner 18 has a tubular configuration with a diameter less than that of elongate tubular member 1 and elongate guide member 17. Additionally, joiner 18 has a centrally located flange 45. When assembled, flange 45 is flush with elongate tubular member 1 and elongate guide member 17 as depicted in FIGS. 1 and 2. Preferably joiner 18 is secured within elongate tubular member 1 and elongate guide member 17 removably slides over joiner 18. In alternate embodiments, either elongate tubular member 1 and elongate guide member 17 are joined directly to one another by any conventional arrangement. For example, elongate tubular member 1 may be tapered at distal end 2 such that elongate guide member 17 is slidably positioned over the tapered portion. Additionally, any similar component suitable for operatively coupling elongate tubular member 1 with elongate guide member 17 will perform satisfactorily in the current invention.

Instrument 100 is not limited to the dimensions and types of material used and configurations described above. Such characteristics of instrument 100 will vary depending on the application or use, for example, the type of surgical procedure, e.g. human or veterinary surgical procedures; size of patient or subject; use for training such as, but not limited to use on mannequins or cadavers; use for demonstrative purposes in various environments such as: commercial settings like trade shows; medical offices; academic settings; or private settings. It should be appreciated that any similar component suitable for satisfactorily performing the function of the corresponding component can be used in the current invention.

Thus, the present invention is well adapted to carry out the objects and attain the ends and advantages mentioned above as well as those inherent therein. While certain embodiments of the invention have been described for the purpose of this disclosure, numerous changes in the construction and arrangement of parts and the performance of steps can be made by those skilled in the art, which changes are encompassed within the scope and spirit of this invention defined by the appended claims.

What is claimed is:

1. An instrument comprising:
    an elongate tubular member having a distal end and a proximal end;
    a user interface coupled to said proximal end, wherein said user interface includes a ball and socket assembly, said ball and socket assembly includes a socket having openings and a ball having protruding arms thereon, said ball disposed within said socket and said protruding arms projecting from said openings of said socket, wherein said openings define a range of motion for said protruding arms;
    an articulating tool assembly coupled to said distal end;
    at least one cabling member extending through the elongate tubular member, said at least one cabling member coupled to at least one of said protruding arms and said cabling member operatively connecting said user interface and said articulating tool assembly such that movement made at said articulating tool assembly directly corresponds to and mimics movement of said user interface.

2. The instrument of claim 1, wherein the user interface further includes a handle assembly operatively connected to the ball and socket assembly, and a support assembly having a first and a second end wall and a plurality of support rails therebetween, wherein said ball and socket assembly is positioned on said support assembly, wherein said proximal end of said elongate tubular member is secured to said first end wall, and wherein said articulating tool assembly includes a dual hinge member having a first side and a second side, a tip assembly pivotally attached to the first side of said dual hinge member, and an elongate guide member pivotally attached to said second side of said dual hinge member.

3. The instrument of claim 2, wherein the handle assembly includes a grip member, and a lever member pivotally coupled to the grip member, wherein actuation of the lever member controls opening and closing of the tip assembly.

4. The instrument of claim 3, wherein said tip assembly is positioned at any location between, and including, fully opened and fully closed by actuation of said lever member.

5. The instrument of claim 4, wherein the distal end of said tip assembly responds to an electrical current by producing heat sufficient to cauterize tissue.

6. The instrument of claim 3, wherein the dual hinge member provides lateral and vertical movement to the tip assembly.

7. The instrument of claim 2, wherein said articulating tool assembly is connected to said distal end of the elongate tubular member by said elongate guide member.

8. A surgical instrument comprising:
    an elongate tubular member having a distal end and a proximal end, wherein said tubular member has a length sufficient to permit position of the distal end within an anatomical cavity while the proximal remains external to the anatomical cavity;

a user interface coupled to the proximal end of said elongate tubular member;

an articulating tool assembly coupled to the distal end of said elongate tubular member and operatively connected to said user interface, wherein movement made at said articulating tool assembly directly corresponds to and mimics movement of said user interface, wherein said user interface includes a handle assembly and a ball and socket assembly directly coupled to said handle assembly, said ball and socket assembly includes a socket having openings and a ball having protruding arms, said ball disposed within said socket and said protruding arms projecting from said openings of said socket, and wherein movement of the handle assembly controls movement of said ball thereby providing lateral and vertical movement of the articulating tool assembly.

9. The instrument of claim 8, wherein the articulating tool assembly includes a dual hinge member having a first side and a second side, a tip assembly pivotally connected to said first side of said dual hinge member, and an elongate guide member pivotally connected to said second side of said dual hinge member.

10. The instrument of claim 9, wherein a distal end of said tip assembly responds to an electrical current by producing heat sufficient to cauterize tissue.

11. The instrument of claim 9, wherein the dual hinge member provides lateral and vertical movement to the tip assembly.

12. The instrument of claim 8, wherein said handle assembly includes a grip member, and a lever member pivotally coupled to the grip member, wherein actuation of the lever member controls opening and closing of the articulating tool assembly.

13. The instrument of claim 12, wherein the user interface further comprises a support assembly carrying said ball and socket assembly.

14. The instrument of claim 8 further comprising at least one cabling member extending through said elongate tubular member, said at least one cabling member operatively connecting said user interface and said articulating tool assembly.

15. A surgical instrument comprising:
an elongate tubular member having a distal end and a proximal end, wherein said elongate tubular member has a length sufficient to permit position of the distal end within an anatomical cavity while the proximal end remains external to the anatomical cavity;
a user interface coupled to the proximal end of said elongate tubular member, wherein the user interface includes a handle assembly, a ball and socket assembly operatively connected to the handle assembly, and a support assembly carrying said ball and socket assembly, said proximal end of the elongate tubular member secured to said support assembly, wherein the ball and socket assembly includes a ball having projecting arms disposed within a socket having openings to allow the projecting arms of the ball to move within the socket, wherein the handle assembly includes a grip member and a lever member operably connected to the grip member, wherein the grip member is directly connected to one of the projecting arms of the ball;
an articulating tool assembly coupled to said distal end of said tubular member and operatively connected to said user interface, wherein movements made at the user interface cause movement of the articulating tool assembly to mimic said movement made at the user interface, the articulating tool assembly including a dual hinge member having a first side and a second side, a tip assembly, said tip assembly pivotally connected to the first side of the dual hinge member, an elongate guide member coupled to the distal end of the elongate tubular member, said elongate guide member having an outwardly extending surface pivotally coupled to the second side of the dual hinge member, wherein the tip assembly includes a base member having a outwardly projecting member pivotally connected to the first side of the dual hinge member, and a moving member pivotally connected to the base member, wherein the moving member is operatively connected to the lever member of the handle assembly thereby permitting opening and closing of the tip assembly.

16. The instrument of claim 15, wherein the grip member and the lever member are pivotally coupled, and wherein actuation of the lever member controls opening and closing of the tip assembly.

17. The instrument of claim 16, wherein said tip assembly is positioned at any location between, and including, fully opened and fully closed by actuation of said lever member.

18. The instrument of claim 17, wherein the distal end of said tip assembly responds to an electrical current by producing heat sufficient to cauterize tissue.

19. The instrument of claim 16, wherein the dual hinge member provides lateral and vertical movement to the tip assembly.

20. The instrument of claim 15, wherein said articulating tool assembly is connected to said distal end of the elongate tubular member by said elongate guide member.

* * * * *